(12) United States Patent
Reicher et al.

(10) Patent No.: US 8,913,808 B2
(45) Date of Patent: *Dec. 16, 2014

(54) SYSTEMS AND METHODS FOR VIEWING MEDICAL IMAGES

(75) Inventors: Murray A. Reicher, Rancho Santa Fe, CA (US); Evan K. Fram, Paradise Valley, AZ (US)

(73) Assignee: DR Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/477,853

(22) Filed: May 22, 2012

(65) Prior Publication Data

US 2013/0169661 A1 Jul. 4, 2013

Related U.S. Application Data

(63) Continuation of application No. 13/228,349, filed on Sep. 8, 2011, now Pat. No. 8,244,014, which is a continuation of application No. 12/702,976, filed on Feb. 9, 2010, now Pat. No. 8,019,138, which is a continuation of application No. 11/179,384, filed on Jul. 11, 2005, now Pat. No. 7,660,488.

(60) Provisional application No. 60/625,690, filed on Nov. 4, 2004.

(51) Int. Cl.
*G06K 9/00* (2006.01)
*G09G 5/36* (2006.01)
*G09G 5/00* (2006.01)
*G09G 5/02* (2006.01)
*G06F 19/00* (2011.01)

(52) U.S. Cl.
CPC ............... *G09G 5/02* (2013.01); *G06F 19/321* (2013.01); *G09G 5/00* (2013.01)
USPC ........................... 382/128; 345/556; 345/581

(58) Field of Classification Search
CPC .................. G06T 7/0012; G06T 2207/30004; G06T 2210/41
See application file for complete search history.

(56) References Cited

U.S. PATENT DOCUMENTS

| | | | |
|---|---|---|---|
| 4,672,683 A | 6/1987 | Matsueda | |
| 5,123,056 A | 6/1992 | Wilson | |

(Continued)

FOREIGN PATENT DOCUMENTS

WO    WO 2007/131157    11/2007

OTHER PUBLICATIONS

Notice of Allowance dated Jul. 20, 2012, in U.S. Appl. No. 13/228,349.

(Continued)

*Primary Examiner* — Joni Richer
(74) *Attorney, Agent, or Firm* — Knobbe, Martens, Olson & Bear, LLP

(57) ABSTRACT

For certain medical images, it is important and/or required that a user view all of a medical image at full resolution so that minute, but important, indicia in the medical image are not missed. A computing systems monitor the portions of the medical image that are displayed on the display device, notates those portions that have been displayed at full resolution (or other user-defined display parameters), and provides the user with information indicating portions that have not been viewed at full resolution and/or provides information indicating for which images of a multiple image examination full pixel display has been accomplished. The process reduces the possibility of missing an abnormality in a medical image due to the viewer not viewing a portion of the image at full resolution or using other user-defined display parameters.

21 Claims, 7 Drawing Sheets

(56) References Cited

U.S. PATENT DOCUMENTS

| | | |
|---|---|---|
| 5,179,651 A | 1/1993 | Taaffe et al. |
| 5,431,161 A | 7/1995 | Ryals et al. |
| 5,452,416 A | 9/1995 | Hilton et al. |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,852,646 A | 12/1998 | Klotz et al. |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,115,486 A | 9/2000 | Cantoni |
| 6,128,002 A | 10/2000 | Leiper |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,243,095 B1 | 6/2001 | Shile et al. |
| 6,269,379 B1 | 7/2001 | Hiyama et al. |
| 6,304,667 B1 | 10/2001 | Reitano |
| 6,347,329 B1 | 2/2002 | Evans |
| 6,351,547 B1 | 2/2002 | Johnson et al. |
| 6,383,135 B1 | 5/2002 | Chikovani et al. |
| 6,388,687 B1 | 5/2002 | Brackett et al. |
| 6,424,996 B1 | 7/2002 | Killcommons et al. |
| 6,438,533 B1 | 8/2002 | Spackman et al. |
| 6,463,169 B1 | 10/2002 | Ino et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,618,060 B1 | 9/2003 | Brackett |
| 6,630,937 B2 | 10/2003 | Kallergi et al. |
| 6,678,764 B2 | 1/2004 | Parvelescu et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,093 B2 | 11/2004 | de la Huerga |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 | 5/2007 | Belykh et al. |
| 7,224,852 B2 | 5/2007 | Lipton et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,505,782 B2 | 3/2009 | Chu |
| 7,526,114 B2 | 4/2009 | Seul et al. |
| 7,526,132 B2 | 4/2009 | Koenig |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,656,543 B2 | 2/2010 | Atkins |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 8,046,044 B2 | 10/2011 | Stazzone et al. |
| 8,065,166 B2 | 11/2011 | Maresh et al. |
| 8,094,901 B1 | 1/2012 | Reicher et al. |
| 8,217,966 B2 | 7/2012 | Fram et al. |
| 8,244,014 B2 | 8/2012 | Reicher et al. |
| 8,292,811 B2 | 10/2012 | Relkuntwar et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0073429 A1 | 6/2002 | Beane et al. |
| 2002/0090124 A1 | 7/2002 | Soubelet et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0180883 A1 | 12/2002 | Tomizawa et al. |
| 2003/0005464 A1 | 1/2003 | Gropper et al. |
| 2003/0016850 A1 | 1/2003 | Kaufman et al. |
| 2003/0028402 A1 | 2/2003 | Ulrich et al. |
| 2003/0037054 A1 | 2/2003 | Dutta et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0140141 A1 | 7/2003 | Mullen et al. |
| 2003/0164860 A1 | 9/2003 | Shen et al. |
| 2003/0184778 A1 | 10/2003 | Chiba |
| 2003/0187689 A1 | 10/2003 | Barnes et al. |

(56) References Cited

U.S. PATENT DOCUMENTS

| | | |
|---|---|---|
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105574 A1 | 6/2004 | Pfaff |
| 2004/0114714 A1 | 6/2004 | Minyard et al. |
| 2004/0143582 A1 | 7/2004 | Vu |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0108058 A1 | 5/2005 | Weidner et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0093198 A1 | 5/2006 | Fram et al. |
| 2006/0093199 A1 | 5/2006 | Fram et al. |
| 2006/0095423 A1 | 5/2006 | Reicher et al. |
| 2006/0095426 A1 | 5/2006 | Takachio et al. |
| 2006/0111941 A1 | 5/2006 | Blom |
| 2006/0171574 A1 | 8/2006 | DelMonego et al. |
| 2006/0181548 A1 | 8/2006 | Hafey |
| 2006/0230072 A1 | 10/2006 | Partovi et al. |
| 2006/0241979 A1 | 10/2006 | Sato et al. |
| 2006/0277075 A1 | 12/2006 | Salwan |
| 2006/0282408 A1 | 12/2006 | Wisely et al. |
| 2007/0050701 A1 | 3/2007 | El Emam et al. |
| 2007/0055550 A1 | 3/2007 | Courtney et al. |
| 2007/0067124 A1 | 3/2007 | Kimpe et al. |
| 2007/0073556 A1 | 3/2007 | Lau et al. |
| 2007/0109402 A1 | 5/2007 | Niwa |
| 2007/0124541 A1 | 5/2007 | Lang et al. |
| 2007/0162308 A1 | 7/2007 | Peters |
| 2007/0174079 A1 | 7/2007 | Kraus |
| 2007/0192140 A1 | 8/2007 | Gropper |
| 2007/0239481 A1 | 10/2007 | DiSilvestro et al. |
| 2008/0059245 A1 | 3/2008 | Sakaida et al. |
| 2008/0100612 A1 | 5/2008 | Dastmalchi et al. |
| 2008/0103828 A1 | 5/2008 | Squilla et al. |
| 2008/0125846 A1 | 5/2008 | Battle et al. |
| 2008/0275913 A1 | 11/2008 | van Arragon et al. |
| 2009/0028410 A1 | 1/2009 | Shimazaki |
| 2009/0123052 A1 | 5/2009 | Ruth et al. |
| 2009/0129643 A1 | 5/2009 | Natanzon et al. |
| 2009/0198514 A1 | 8/2009 | Rhodes |
| 2010/0053353 A1 | 3/2010 | Hunter et al. |
| 2010/0138239 A1 | 6/2010 | Reicher et al. |
| 2010/0198608 A1 | 8/2010 | Kaboff et al. |
| 2010/0201714 A1 | 8/2010 | Reicher |
| 2010/0299157 A1 | 11/2010 | Fram et al. |
| 2011/0016430 A1 | 1/2011 | Fram |
| 2011/0110572 A1 | 5/2011 | Guehring et al. |
| 2011/0267339 A1 | 11/2011 | Fram |
| 2011/0316873 A1 | 12/2011 | Reicher |
| 2012/0163684 A1 | 6/2012 | Natanzon et al. |
| 2012/0194540 A1 | 8/2012 | Reicher |
| 2013/0083023 A1 | 4/2013 | Fram |
| 2013/0159019 A1 | 6/2013 | Reicher |

OTHER PUBLICATIONS

Interview Summary dated Jul. 31, 2012 in U.S. Appl. No. 13/171,081.
Interview Summary dated Jun. 28, 2012 in U.S. Appl. No. 11/944,027.
Final Office Action dated Aug. 6, 2012 in U.S. Appl. No. 12/622,404.
US 7,801,341, 9/2010, Fram et al. (withdrawn).
US 8,208,705, 6/2012, Reicher et al. (withdrawn).
Crowley, Rebecca et al., *Development of Visual Diagnostic Expertise in Pathology: an Information-processing Study*, Jan. 2003, Journal of the American medical Informatics Association, vol. 10, No. 1, pp. 39-51.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated May 14, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.

(56) References Cited

OTHER PUBLICATIONS

Notice of Allowance dated May 26, 2011 in U.S. Appl. No. 11/265,979.
Office Action dated Jun. 8, 2012 in U.S. Appl. No. 13/171,081.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, 2012 in U.S. Appl. No. 13/079,597.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Mendelson, et al., "Informatics in Radiology—Image Exchange: IHE and the Evolution of Image Sharing," RadioGraphics, Nov.-Dec. 2008, vol. 28, No. 7.
Notice of Allowance dated May 17, 2010, in U.S. Appl. No. 11/268,261.
Supplemental Notice of Allowance dated Aug. 6, 2010, in U.S. Appl. No. 11/268,261.
Office Action dated Aug. 23, 2013, in U.S. Appl. No. 12/857,915.
Interview Summary dated Feb. 4, 2014, in U.S. Appl. No. 12/857,915.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Non-Final Office Action dated Apr. 4, 2013 in U.S. Appl. No. 13/535,758.
Notice of Allowance, dated Aug. 23, 2013 in U.S. Appl. No. 13/535,758.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Mar. 13, 2014 in U.S. Appl. No. 11/942,687.
Final Office Action dated Oct. 22, 2012 in U.S. Appl. No. 11/944,027.
Notice of Allowance dated Jun. 5, 2013 in U.S. Appl. No. 11/944,027.
Appeal Brief dated Mar. 4, 2013 in U.S. Appl. No. 11/944,000.
Examiner's Answer dated Jun. 26, 2013 in U.S. Appl. No. 11/944,000.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Notice of Allowance dated Jul. 3, 2014, in U.S. Appl. No. 12/857,915.
Interview Summary, dated Jun. 17, 2014 in U.S. Appl. No. 11/942,687.
Action, dated Jul. 18, 2014 in U.S. Appl. No. 11/942,687.

SYSTEMS AND METHODS FOR VIEWING MEDICAL IMAGES

CROSS-REFERENCE TO RELATED APPLICATIONS

This application is a continuation of U.S. patent application Ser. No. 13/228,349, filed on Sep. 8, 2011 and entitled "SYSTEMS AND METHODS FOR VIEWING MEDICAL IMAGES," which is a continuation of U.S. patent application Ser. No. 12/702,976, filed on Feb. 9, 2010 and entitled "SYSTEMS AND METHODS FOR VIEWING MEDICAL IMAGES," now U.S. Pat. No. 8,019,138, which is a continuation of U.S. patent application Ser. No. 11/179,384, filed on Jul. 11, 2005 and entitled "SYSTEMS AND METHODS FOR VIEWING MEDICAL IMAGES," now U.S. Pat. No. 7,660,488, which claims priority under 35 U.S.C. §119(e) to U.S. Provisional Application Ser. No. 60/625,690, filed on Nov. 4, 2004, each of which is hereby expressly incorporated by reference in its entirety.

BACKGROUND OF THE INVENTION

1. Field of the Invention

This invention relates to management and viewing of medical images and, more particularly, to systems and methods of tracking which portions of medical images have been displayed using predetermined display parameters.

2. Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. Accordingly, there is a need for improved systems and methods of viewing and manipulating these digital images.

SUMMARY OF THE INVENTION

A pixel is the smallest changeable element of a digital image, where an image comprises a plurality of pixels. For example, a mammographic image may include an array of 4,000 horizontal by 6,000 vertical pixels. For all medical images, particularly for certain modalities such as mammography, for example, it is important that every image pixel is displayed on a display device and viewed by a viewer or reader, such as a doctor, nurse, or other medical staff member. For example, in the field of mammography, diagnosis of a cancer may only be detectable in a small number of pixels. Accordingly, if this small number of pixels is not viewed by the viewer or reader, a misdiagnosis may be given to the patient. If a mammography image comprises 16 million pixels (e.g., an image resolution of 4,000×4,000), all of the 16 million pixels cannot be simultaneously displayed on a display device with a resolution of 2,048×1,536 (a 3.2 Megapixel display). Thus, only about ⅕ of the 16 million pixels of the mammography image may be displayed simultaneously at full resolution on such a display device. In other words, if one elects to display the image at full resolution, the entire 4,000×4,000 pixel image cannot be simultaneously displayed on a 2,048×1,536 or smaller matrix monitor. If one elects to display the complete area of the image, the only alternative is to display the entire image at a reduced resolution, discarding a fraction of the pixels.

Because an entire medical image cannot be concurrently viewed at full resolution on a typical display device, software applications currently allow viewing of portions of medical images at full resolution on the display device. In some embodiments, a user may be required to adjust the portion of the medical image that is displayed at full resolution on the display device in an attempt to view all of the image pixels. For example, the viewer may select up to hundreds of portions of the image for sequential viewing at full resolution before the entire image has been viewed at full resolution. As those of skill in the art will appreciate, manually tracking which portions of an image have been viewed at full resolution is cumbersome and may not allow the viewer to accurately determine when all relevant portions of the image have been viewed at full resolution. Currently, there are no systems or methods for automatically tracking the portions of a medical image that have been displayed at full resolution, or for indicating those images for which all pixels have been presented on a display device at full resolution. Accordingly, portions of medical images may not be viewed at full resolution and important indicia in the medical image may be overlooked. Thus, systems and methods for tracking portions of a medical image that have been viewed at full resolution are desired. Furthermore, systems and methods for allowing a viewer of the medical image to visually distinguish those portions that have not been viewed at full resolution are desired.

In one embodiment, the invention comprises a method of viewing medical images on a display device coupled to a computing system, wherein the display device is configured to concurrently display N pixels of an image to a user. In one embodiment, the method comprises (a) receiving an image at the computing system, wherein the image comprises M pixels, wherein M is greater than N; (b) displaying on the display device a portion of the image comprising N pixels, wherein the image portion is displayed at full resolution; (c) determining whether each of the M pixels of the image has been displayed on the display device, and (d) in response to determining that not all of the M pixels of the image have been displayed on the display device, returning to step (b).

In another embodiment, the invention comprises a method of viewing a mammographic image in a viewing pane depicted on a display device, wherein the viewing pane is configured to display a predetermined number of pixels. In one embodiment, the method comprises displaying the mammographic image at a reduced resolution in the viewing pane, displaying a portion of the mammographic image at full resolution in the viewing pane, and displaying the mammography image at the reduced resolution in the viewing pane, wherein a portion of the reduced resolution image that corresponds with the portion of the mammographic image that was displayed at full resolution is visually distinguishable from the remaining portion of the reduced resolution image.

In another embodiment, the invention comprises a computing system for viewing a mammographic image. In one embodiment, the system comprises a display device depicting a viewing pane, means for displaying a portion of the mammographic image at full resolution in the viewing pane, and means for displaying the entire mammographic image at the reduced resolution in the viewing pane, wherein the portion of the mammographic image displayed at full resolution is visually distinguishable from the other portions of the reduced resolution mammographic image.

In another embodiment, the invention comprises a computing system for viewing a medical image. In one embodiment, the system comprises a display device having a predetermined number of pixels, an input interface configured to receive the medical image, an application module comprising software for initiating display of the medical image on the display device, and a processing unit configured to execute the software, wherein, in a first mode, the software initiates display of the entire medical image at a reduced resolution on the display device, in a second mode, the software initiates display of a portion of the medical image at full resolution on the display device, and, in a third mode, the software initiates display of the entire medical image at the reduced resolution on the display device, wherein a portion of the reduced resolution medical image corresponding to the portion of the medical image displayed at full resolution is visually distinguishable from the remaining portions of the reduced resolution medical image.

In another embodiment, the invention comprises a method of viewing medical images. In one embodiment, the method comprises selectively viewing portions of a high resolution image and verifying that the entire high resolution image has been viewed.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
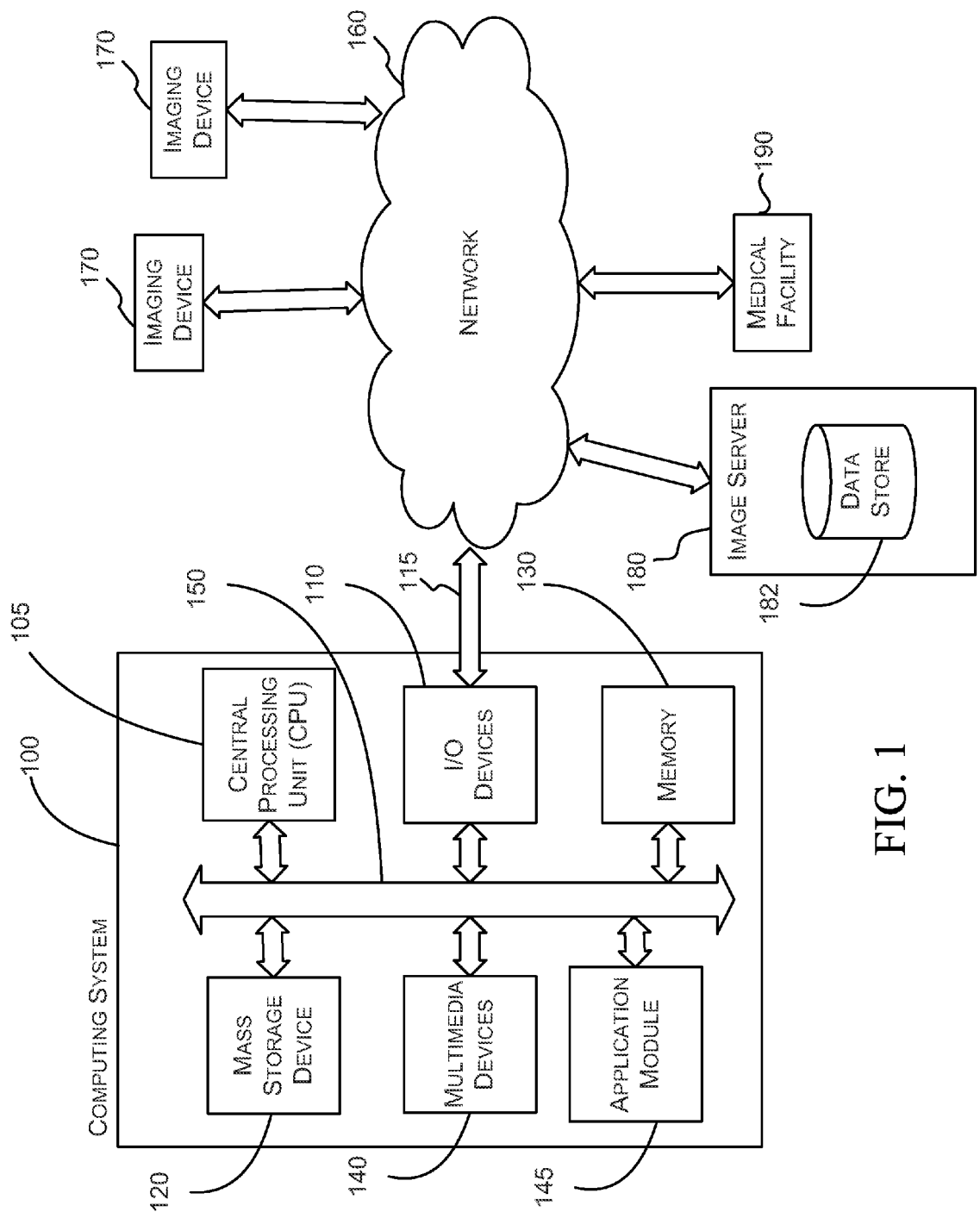
FIG. 1 is a block diagram of an exemplary computing system in communication with a network and various networked devices.

FIG. 1 is a block diagram of an exemplary computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

The computing system 100 includes, for example, a personal computer that is IBM, Macintosh, or Linux/Unix compatible. In one embodiment, the exemplary computing system 100 includes a central processing unit ("CPU") 105, which may include a conventional microprocessor, an application module 145 that comprises one or more various applications that may be executed by the CPU 105. The application module 145 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server via the network 160 and image information is transmitted to the image server 160 and stored in the data store 182. In one embodiment, the image data is stored in Digital Imaging and Communications in Medicine ("DICOM") format. The complete DICOM specifications may be found on the National Electrical Manufactures Association Website at <medical.nema.org>. Also, *NEMA PS 3—Digital Imaging and Communications in Medicine,* 2004 ed., Global Engineering Documents, Englewood Colo., 2004, provides an overview of the DICOM standard. Each of the above-cited references is hereby incorporated by reference in their entireties. In one embodiment, the data store 182 also stores the user-defined display parameters associated with one or more of the images stored on the data store 182. As discussed in further detail below, the user-defined display parameters may vary depending of the type of image, area imaged, clinical indication, source of image, display device, user, or other factors. Accordingly, any type of user-defined display parameter is expressly contemplated for use in conjunction with the systems and methods described herein.

The exemplary image server 160 is configured to store images from multiple sources and in multiple formats. For example, the image server 160 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

DEFINITION OF TERMS

Below is a definition of certain terms used herein.

"Medical image" is defined to include an image of an organism. It may include but is not limited to a radiograph, computed tomography (CT), magnetic resonance imaging (MRI), Ultrasound (US), mammogram, positron emission tomography scan (PET), nuclear scan (NM), pathology, endoscopy, ophthalmology, or many other types of medical images. While this description is directed to viewing and tracking of medical images, the methods and systems described herein may also be used in conjunction with non-medical images, such as, images of circuit boards, airplane wings, and satellite images, for example.

"Modality" is defined as a medical imaging device (a patient who undergoes an MRI is said to have been examined with the MRI modality).

"Patient" refers to an individual who undergoes a medical imaging examination.

"Viewing" is defined to include the process of visually observing one or more medical images associated with exams.

"Viewer" is defined as any person who views a medical image.

"Reading" is defined to include the process of visually observing one or more medical images for the purpose of creating a professional medical report, also called an interpretation. When reading is complete, an exam may be labeled "read," indicating that the medical professional has completed observation of the one or more medical images for purposes of creating a medical report.

"Reader" is defined to include one who is authorized to perform the reading process.

"User" is defined to include any person that is a viewer and/or a reader.

"Display parameters" are defined to include methods of display of an image or exam. For example, an image or exam may be displayed with a certain pixel window level or width (similar to brightness and contrast), in color, based on a certain color map, opacity map, or other display parameters.

"Full pixel display" is defined to include display on a monitor or other display system of every pixel of a medical image.

"Full Resolution" is defined to include the concurrent display of all pixels of a medical image portion on a display device.

"Reduced Resolution" is defined to include display of less than all of the pixels of a medical image portion on a display device.

Figure 2:
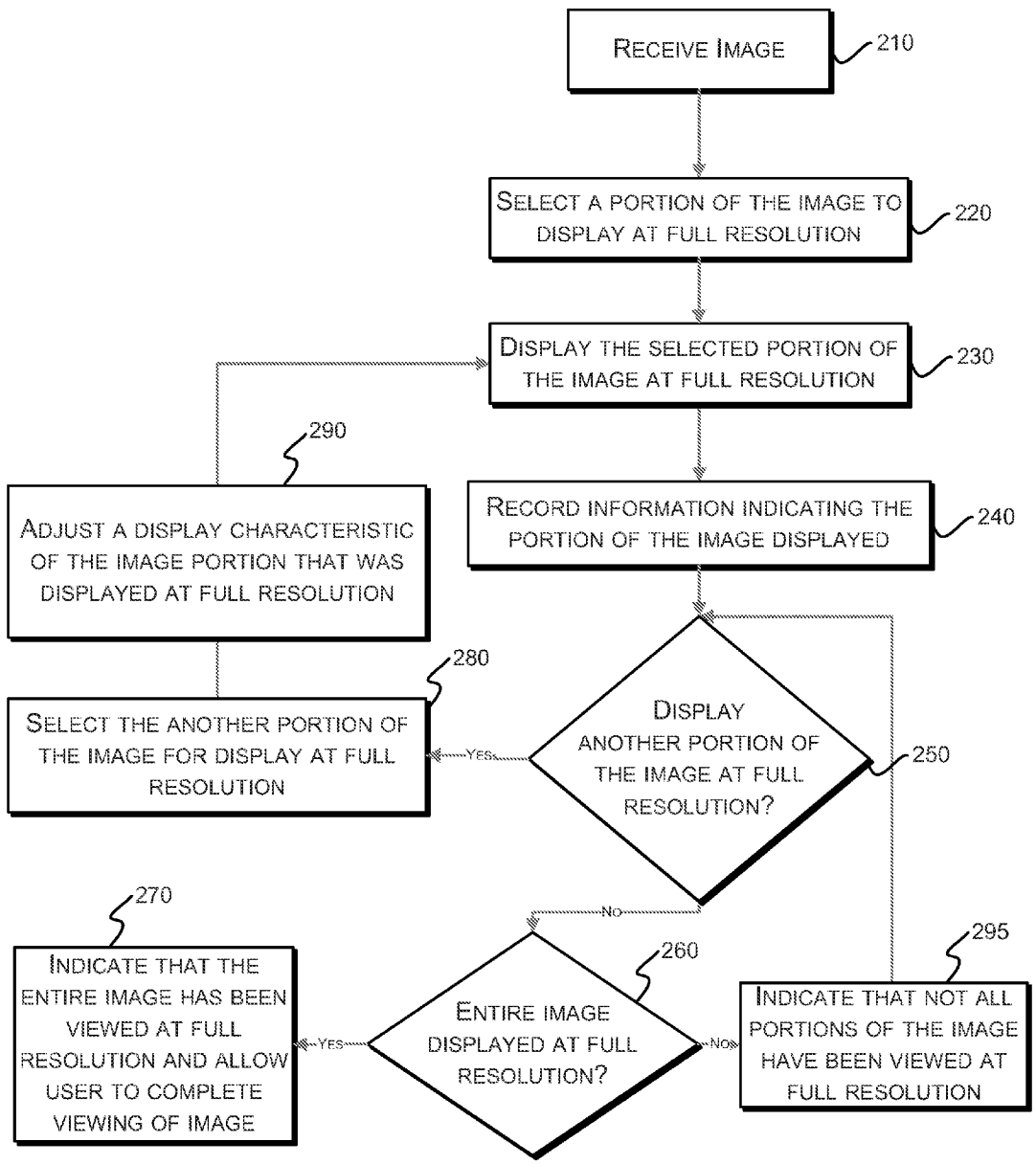
FIG. 2 is a flowchart illustrating a method of tracking which portions of a medical image have been displayed at full resolution.

"User-defined display parameter" refers to rules that a user can establish and store in a database that establish criteria for image display that is considered adequate. For example, a user-defined display parameter might store a rule that triggers certain warnings or displays if all pixels are not displayed or alternatively if at least half the pixels are not displayed, or alternatively, if some determined fraction of the pixels are not viewed with a certain display method (such as image window, level, brightness, contrast, opacity, color look-up table, or other parameters). User-defined display parameters may also refer to other image processing functions, such as edge enhancement and automated image analysis functions, e.g., computer-aided detection (CAD) techniques FIG. 2 is a flowchart illustrating a method of tracking which pixels of a medical image have been displayed according to user-defined display parameters. In one embodiment, the method described with respect to FIG. 2 is performed by a computing system 100, a medical facility 190, or an image server 190, for example. For ease of description, the method will be discussed below with reference to a computing system 100 performing the method. Depending on the embodiment, certain of the blocks described below may be removed, others may be added, and the sequence of the blocks may be altered.

In one embodiment, the user-defined display parameters specify that an entire medical image must be viewed at full resolution before a reader may mark the image as read. However, the user-defined display parameters may have different requirements, such as requiring that at least a defined portion of the pixels are displayed at full resolution and/or a defined portion of the pixels are viewed with a certain display method, for example. In another embodiment, the user-defined display parameters may specify that the medical image is viewed at a resolution that is less than full resolution. In other embodiments, the user-defined display parameters may specify additional display settings that must be satisfied in order to allow the reader to mark the image as read. For example, the display parameters may be set to require that every $n^{th}$ pixel is displayed. Thus, various user-defined display parameters may be established on a user, modality, or facility basis, for example. In one embodiment, such as when viewing CT images, the display parameters specify that the CT images must be viewed using a specified series of display parameters, such as lung windows, bone windows, and/or other types of windows, for example. In this embodiment, if the user forgets to view the images separately using all the required display parameters, the CT images may be misinterpreted. For ease of description, the following description refers to user-defined display parameters specifying that every pixel of the image is displayed at full resolution before it may be marked as read. However, the methods described herein are not limited to these display parameters and application of these methods using other user-defined display parameters are expressly contemplated. Any reference to tracking pixels at full resolution should be interpreted to cover similar systems and methods for monitoring and/or tracking of any other user-defined display parameter or combination of display parameters.

In some embodiments, it may be important and/or required that a user view all of a medical image at full resolution. Thus, a user may be required to adjust the portion of the medical image that is displayed at full resolution on the display device in an attempt to view all of the image pixels. However, currently there are no systems or methods for automatically tracking the portions of a medical image that have already been displayed at full resolution, or for indicating those images for which all pixels have been presented on a display device at full resolution ("full pixel display"). Accordingly, there is a need for image viewing devices and computing systems that monitor the portions of the medical image that are displayed on the display device, notate those portions that have been displayed at full resolution (or other user-defined display parameters), and provide the user with information indicating portions that have not been viewed at full resolution and/or provide information indicating for which images of a multiple image examination full pixel display has been accomplished. These processes are referred to herein as "visual pixel tracking."

In one embodiment, visual pixel tracking applies to the display of an individual image. In another embodiment, visual pixel tracking applies to a volume rendering, wherein after 3-D slicing, the computing system 100 indicates which pixels in a volume have not been displayed at full resolution or meeting other user-defined display parameters. FIG. 2, described in detail below, is a flowchart illustrating an exemplary method of tracking which pixels of a medical image are displayed according to user-defined display parameters. When volume rendering is performed, the method of FIG. 2 may be applied to each slice of the imaging volume. The user interface may provide a real time status of viewing each of the slices at full resolution.

In one embodiment, the computing system 100 is configured to determine a portion of the medical image on which visual pixel tracking is to be applied. Many medical images comprise areas surrounding the area of interest that are not important for a user, such as a doctor, to view and mark as read. For example, a medical image of a breast typically includes areas, such as air around the breast, that are irrelevant to the analysis by the user. Accordingly, viewing of these irrelevant portions of the image according to the user-defined display parameters is not necessary. In one embodiment, the computing system 100 analyzes the medical image and determines those areas that are irrelevant to the user's analysis. These irrelevant areas are then excluded from the user-defined display parameters and a viewer may mark an image as read without viewing the irrelevant areas at full resolution, for example. In another embodiment, the user may define the irrelevant areas of an image prior to viewing portions of the image at full resolution. For example, the user may use the keyboard, mouse, or other input device, to select areas surrounding the area of interest that do not require viewing according to the user-defined display parameters. In yet another embodiment, the user may determine that the relevant portions of an image have been viewed according to the display parameters, without the need to pre-select portions that should be viewed according to the display parameters. By providing for automatic and/or manual selection of irrelevant portions of a medical image, the viewer is not required to display those irrelevant portions of the medical image according to the user-defined display parameters, such as full resolution.

In a block 210, one or more medical images are received from an image source. Although the process described below is directed to processing one image, it is possible to use the process in conjunction with multiple images. The image source may comprise one or more of the imaging devices 170, the image server 180, the medical facility 190, or any other device that is capable of transmitting medical images. The medical image may be received via the network 160, or by other means, such as transferred on a floppy disk or CD-ROM. For ease of description, in the description that follows the exemplary computing system 100 will be the device that receives and displays the medical image. However, other computing devices may perform the methods described herein. The received medical image comprises more pixels that the display device and, thus, the entire image may not be concurrently displayed at full resolution.

Continuing to a block 220, a portion of the medical image is selected for display on the display device. As discussed above, many medical images contain more pixels than are capable of being displayed concurrently on a display device. Accordingly, the user of the medical image may select a portion of the image to display at full resolution on the display device. Alternatively, the computing system 100 may automatically determine a portion of the image to display on the display device. For example, in one embodiment the computing system 100 may initially display a top, left portion of received medical image first and then proceed to display adjacent portions of the image in response to an input from the user.

Moving to a block 230, the portion of the image that was selected for display at full resolution is displayed on the display device. More particularly, all of the image pixels for the selected portion of the medical image are concurrently displayed on the display device. In one embodiment, depending on the resolution of the medical image and the resolution of the display device, about 1-25% of the image may be concurrently displayed at full resolution on the display device.

Continuing to a block 240, an indication of the portion of the image that is displayed at full resolution is recorded. For example, if ⅛ of the total pixels of an image are displayed at full resolution, an indication of these pixels is recorded, such as by storing pixel information in a memory 130 of the computing system 100. Alternatively, the information regarding displayed pixels may be stored on a central server, such as the image server 180, which may then be accessible to other medical facilities and imaging devices.

In a decision block 250, the computing system 100 determines if another portion of the image has been selected for display at full resolution. In one embodiment, the user is presented with a reduced resolution representation of the medical image and is allowed to select another portion of the image for display at full resolution. Selection of an image portion may be accomplished by pressing certain keys on a keyboard, such as the arrow keys, for example. In another embodiment, the user may change the selected portion for viewing by moving a mouse, or other input device. For example, a pan tool may be invoked by the user, allowing the user to adjust the portion of the image displayed at full resolution so that areas of the images that are above, below, or to the sides of the current displayed portion are displayed at full resolution. In another embodiment, the computing system 100 may be configured to periodically updated the display with a portion of the image that has not yet been displayed at full resolution, or update the display in response to an input from the user.

If in the decision block 250, the computing device 100 determines that instructions have been received to display another portion of the image on the display device, at a block 280 the requested portion of the image is selected for display at full resolution. In one embodiment, such as when a panning tool is used, the selected portion comprises much of the currently displayed portion of the image. In another embodiment, the selected portion comprises a portion of the image that is entirely different than the portion of the image that is currently displayed.

Moving to a block 290, one or more display characteristics of the selected portion of the image that is displayed at full resolution is altered. Thus, when the entire image is displayed on the display device at a reduced resolution, those portions of the image that have not been displayed at full resolution can be identified. These portions of the image may then be selected for display at full resolution.

In one embodiment, the adjustment of a display characteristic comprises changing a color of the image portion. In another embodiment, other indicators, such as a line surrounding those image portions already displayed at full resolution, may be used to discriminate between portions of the image that have been displayed at full resolution and portions that have not been displayed at full resolution. Accordingly, when the entire image is viewed at a reduced resolution, such as by displaying only every $n^{th}$ image pixel, where n is less than or equal to the ratio of image pixels to display pixels, areas of the image that have not been viewed at full resolution are distinguished from those that have been viewed at full resolution. Based on the distinguishing display characteristic, the user may select for display a portion of the image that has not yet been displayed at full resolution. In one embodiment, coloring of the viewed pixels may be toggled on and off by the user. In another embodiment, a text message, icon, or other indication, may be displayed at the bottom of the display, for example, indicating that the image has been viewed according to the user-defined display parameters. In yet another embodiment, the outside margins of the viewing pane may change color or the system could beep or provide some other audible feedback when the image has been displayed according to the user-defined display parameters.

Moving from block 290, the selected portion of the image is displayed at full resolution in block 230, and the method continues to block 240 and block 250. Accordingly, blocks 230, 240, 250, 280, and 290 may be repeated multiple times in the process of selecting and displaying portions of an image at full resolution.

Referring again to the decision block 250, if the computing device 100 determines that instructions to display another portion of the image at full resolution have not been received, the method continues to a decision block 260, wherein the computing device 100 determines whether all of the image has been displayed at full resolution. If it is determined that not all of the image has been displayed at full resolution, the method continues to a block 295, wherein an indication is provided to the user that not all of the image has been viewed at full resolution. If, however, in the decision block 260, the computing device 100 determines that the entire image has been displayed at full resolution, the method continues to a block 270, wherein an indication is provided to the user that the entire image has been displayed at full resolution.

As noted above, the flowchart of FIG. 2 illustrates an exemplary process of tracking pixels viewed by a user according to exemplary user-defined display parameters. In particular, the user-defined display parameters in the example of FIG. 2 specify that the entire image is viewed at full resolution. However, in other embodiments the user-defined display parameters may require that, for example, only a portion of the image is displayed at full resolution, or any other predetermined reduced resolution. For example, many images contain non-rectangular areas of interest. The portions outside of the areas of interest, such as a breast in a mammography image, may include air, other body portions, or imaging equipment, for example. Those of skill in the art will recognize that is not important to analyze every pixel of the air surrounding an area or interest. Accordingly, in one embodiment, the user or the software may select portions of the image that must be displayed according to the user-defined display parameters. In another embodiment, the display parameters may specify that the viewer determines when the image has been viewed according to the user-defined display parameters. In this embodiment, the system may track the viewed pixel of the image, present the viewer with a view of the image that distinguishes portions of the image that have not been viewed at full resolution, or according to any other user-defined display parameters, and the viewer can determine whether the image can be marked as read.

In one embodiment, the user can establish user-defined display parameters and store those parameters in a database. For example, the user may establish a rule linked to the individual user, user type, exam type, modality, system or other links that triggers the above described automatic warnings and/or visual pixel tracking if a user-defined fraction of the pixels are displayed. The user may, alternatively or additionally, establish other rules linked to the individual user, user type, exam type, modality, and/or system that trigger the above-described automatic warnings and/or visual pixel tracking if an image is not viewed using one or more specified display parameters or combination of display parameters. For example, the computing system 100 may be configured to automatically direct the user to any pixels or images that have not been displayed with specific display parameters.

In another embodiment, rules may be generated to automatically designate when the pixel tracking process should be turned on and off. For example, rules may designate that visual pixel tracking applies to only certain viewers or users. In one embodiment, one type of display parameters can apply to one modality and another set of display parameters can apply to another modality.

In one embodiment, the user is not able to notate an image as being read, or completely viewed, until the entire image has been displayed at full resolution. Accordingly, in the exemplary method of FIG. 2, if not all of the image has been displayed at full resolution, the method indicates that the entire image has not been viewed at full resolution in block 295, and the method returns to block 250, wherein another portion of the image may be selected for viewing.

In one embodiment, the computing system 100 automatically displays portions of the image that have not yet been displayed at full resolution, and/or that have not been displayed such that user-defined display parameters have been met. For example, a user interface may include visual indications as to which portions of an image include pixels that have not been displayed, or which pixels have not been displayed using a user-defined display parameter, such as a specified window or level setting. In one embodiment, the computing system 100 automatically displays a message indicating which one or more of several images has not displayed with full pixel display and/or meeting user-defined display parameter criteria. In another embodiment, the computing system 100 automatically directs the user to any image positions or images, that have not been displayed at full resolution and/or meeting user-defined display parameter criteria.

Figure 3:
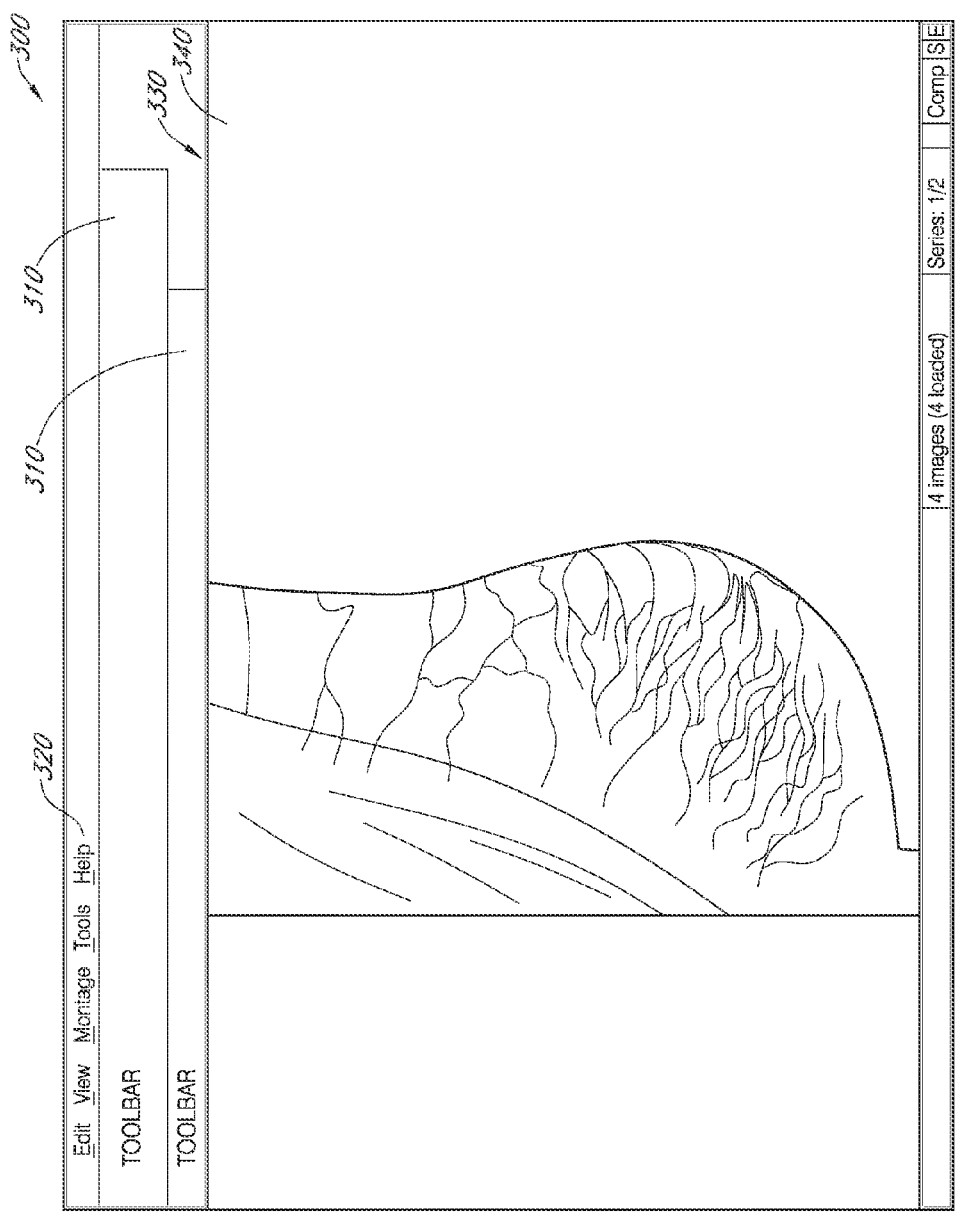
FIG. 3 is a mammographic image, wherein the entire medical image is displayed at a reduced resolution.

FIG. 3 is an exemplary graphical user interface (GUI) 300 including a menu bar 320, multiple toolbars 310, and an image viewing pane 330. In the example of FIG. 3, a mammographic image is displayed in the viewing pane 330, wherein the entire image is displayed at a reduced resolution. For example, if the mammography image comprises 16 million pixels (e.g., an image resolution of 4,000×4,000), all of the 16 million pixels cannot be simultaneously displayed on a display device with a resolution of 2,048×1,536 (a 3.2 Megapixel display). Thus, only about ⅕ of the 16 million pixels of the mammography image may be displayed simultaneously at full resolution on such a display device. Accordingly, in order to view the entire mammographic image on a display device, the number of pixels in the image is reduced by removing about 4 of every 5 pixels. Those of skill in the art will recognize that there are many systems and methods for reducing the resolution of a digital image. These systems and methods are contemplated for use in generating a reduced resolution image, such as the image displayed in the viewing pane 330 of FIG. 3.

As noted above, because many medical images, such as mammography images, for example, may include features or abnormalities that are only detectable by viewing only 1, or a few, pixels, a viewer of the image 340 may not be able to detect all features and abnormalities. Importantly, the viewer of a mammographic image displayed at less than full resolution, such as image 340, may not be able to detect an abnormality related to breast cancer. For example, the area 350 shown in FIG. 3 may include many times more pixel than are displayed in the area 350.

Figure 4:
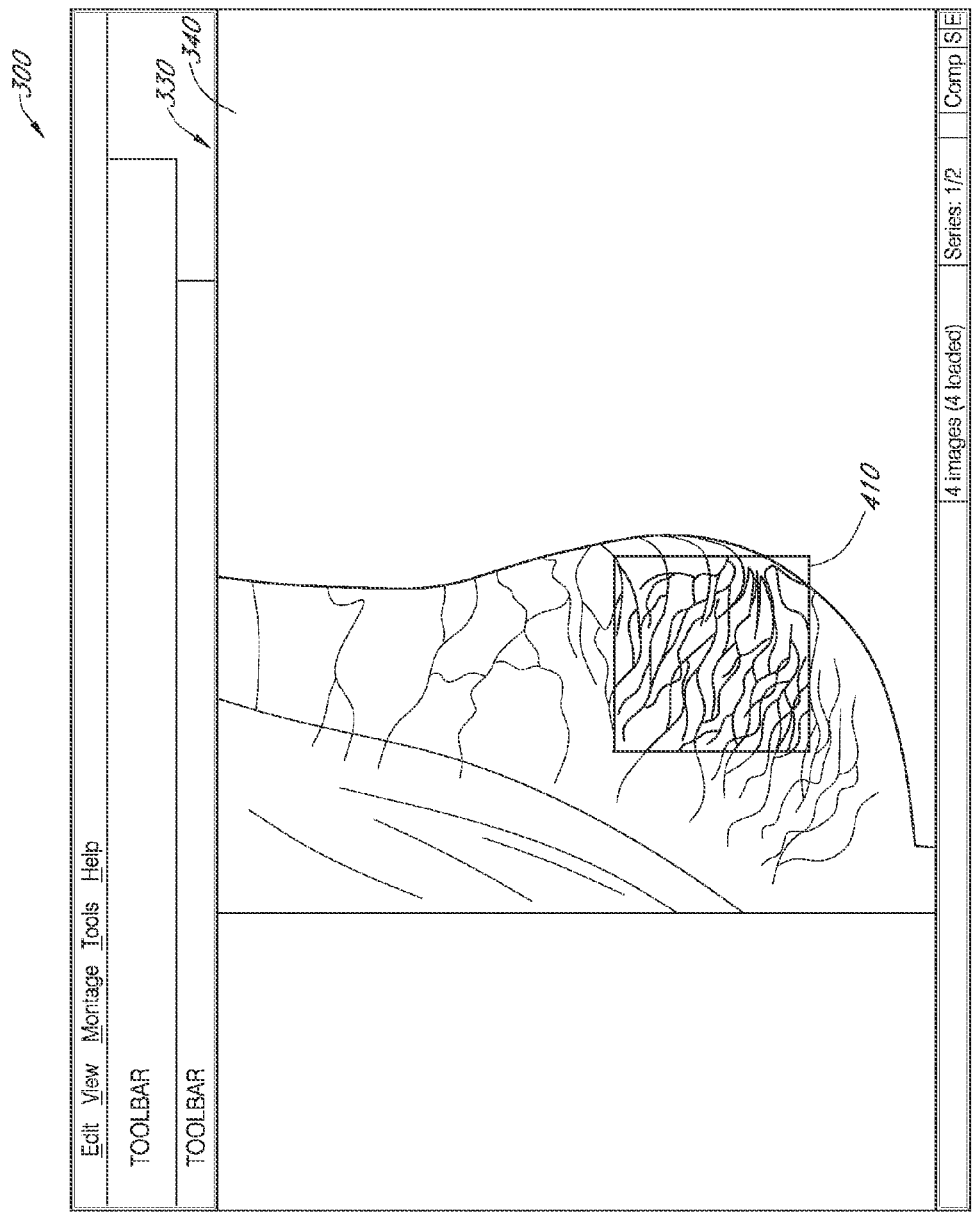
FIG. 4 is the mammographic image of FIG. 3, wherein a portion of the mammographic image is displayed at full resolution.
Figure 5:
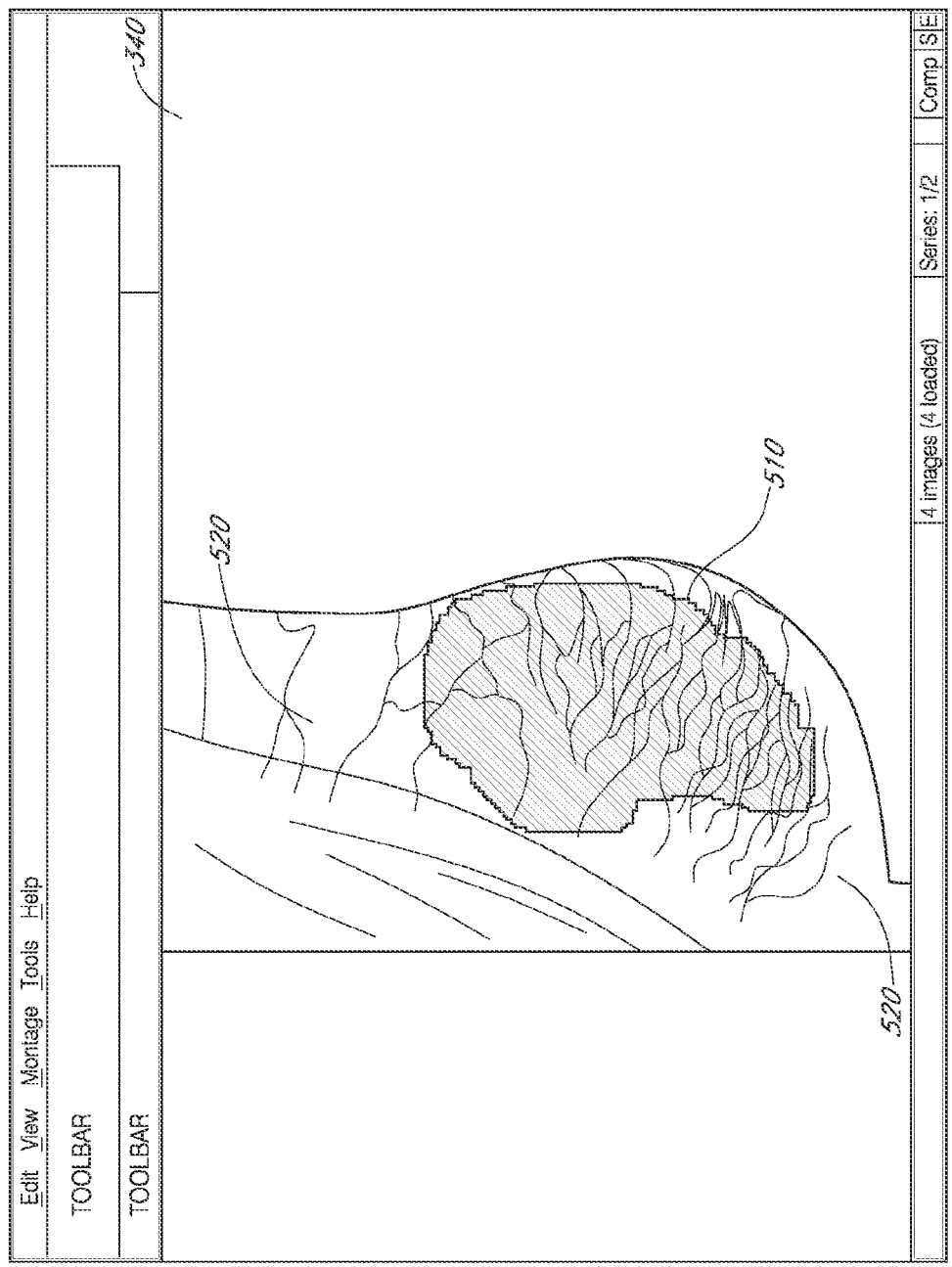
FIG. 5 is the mammographic image of FIG. 3, wherein portions of the image that have been displayed at full resolution are color inverted.

FIGS. 4 and 5 illustrate a method of sequentially viewing portions of a medical image at full resolution and related methods of tracking and indicating the portions of the image that have been viewed at full resolution. In the embodiment of FIGS. 4 and 5, the reduced resolution image remains in the viewing pane 330 while a portion of the image is also displayed at full resolution within the viewing pane 330.

FIG. 4 is the GUI 300 with the mammographic image 340 (FIG. 3) displayed in the viewing pane 330 at a reduced resolution, where a window 410 displays a portion of the image at full resolution. In one embodiment, the portion of the mammographic image that is displayed at full resolution in the window 410 is selected by the user, such as by allowing the user to move a cursor, or other icon, over portions of the mammographic image. In this embodiment, when the cursor is over an area of the mammographic image, the window 410 displays at full resolution the portion of the mammographic image currently covered by the cursor. Thus, in the example of FIG. 4, the window 410 display all of the pixels of a portion of the reduced resolution image 340.

In one embodiment, the portion of the image displayed at full resolution in the window 410 is updated as the user moves the cursor across the reduced resolution mammographic image 340. Thus, the user may determine the order in which portions of the reduced resolution image are viewed at full resolution and may control the speed at which portions of the image are viewed at full resolution.

FIG. 5 is the GUI 300 with the reduced resolution mammographic image 340 (FIG. 3) displayed in the viewing pane 330, wherein portions of the image that have been displayed at full resolution are distinguished from portions of the image that have not yet been displayed at full resolution. In the embodiment of FIG. 5, for example, the portions of the image that have already been viewed at full resolution, such as via the window 410 (FIG. 4) are color inverted from those portions that have not been viewed at full resolution. In FIG. 5, the non-inverted image portion 510 indicates that this portion has been displayed at full resolution. The inverted image portion 520, which substantially surrounds the non-inverted image portion 510, indicates that portion 520 has not been viewed at full resolution. Accordingly, if the viewer is required to view all of the image at full resolution, the portion 520 would need to be viewed at full resolution.

In another embodiment, the portions of the image that have been viewed at full resolution are distinguished from those portions that have not been viewed at full resolution in other manners. For example, in one embodiment a border may be displayed around those portions of the image 340 that have been displayed at full resolution. In another embodiment, the portion that has been viewed at full resolution is color-inverted. In another embodiment, the coloring of the portion that has been viewed at full resolution is adjusted, such as by adding a yellow tint to that portion.

Figure 6:
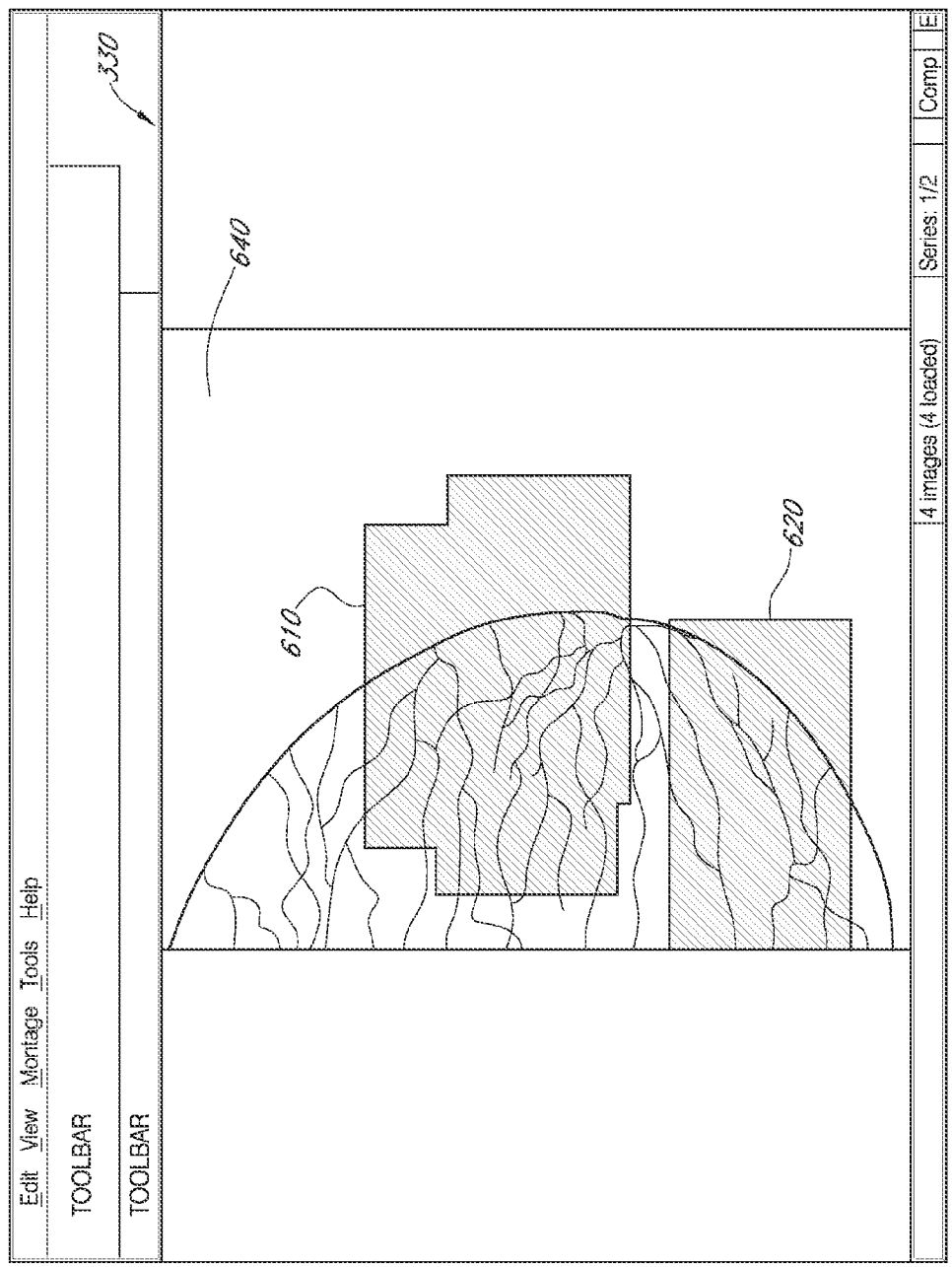
FIG. 6 is an exemplary mammographic image, wherein a portion of the image has been selected for display at full resolution and another portion of the image has already been displayed at full resolution.
Figure 7:
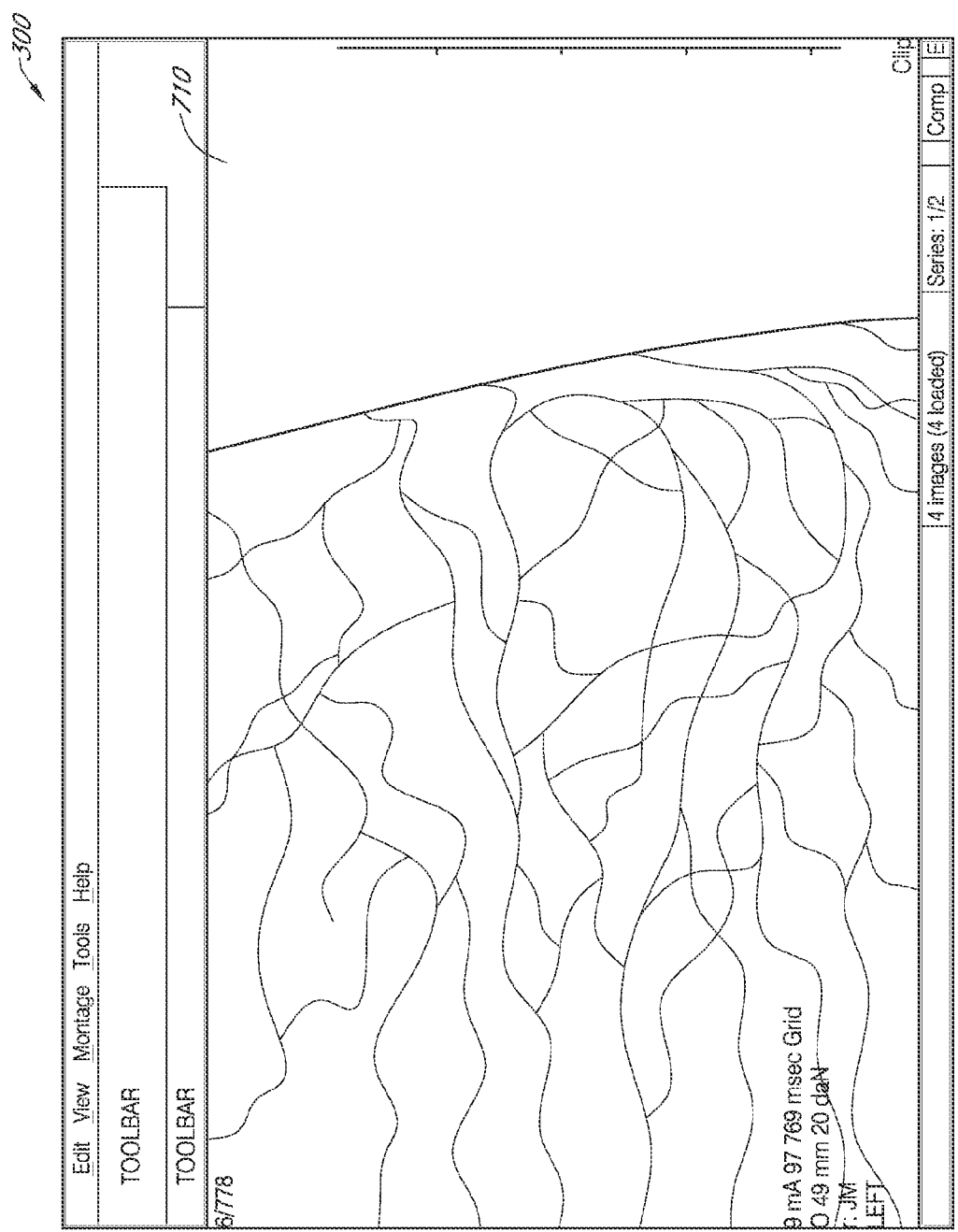
FIG. 7 is a portion of a mammographic image that has been selected for display at full resolution displayed at full resolution.

FIGS. 6 and 7 illustrate another method of sequentially viewing portions of a reduced resolution medical image at full resolution and related methods of tracking and indicating the portions of the image that have been viewed at full resolution.

FIG. 6 is the GUI 300 with the reduced resolution mammographic image 640 displayed in the viewing pane 330, wherein a portion of the image has already been displayed at full resolution and another portion of the image is selected for display at full resolution. More particularly, the inverted portion 610 of the image (shaped generally as two overlapping rectangles), indicates that portion 610 has already been displayed at full resolution. As described above, other methods of indicating portions of an image that have been viewed at full resolution may be used also.

In one embodiment, a portion of the mammographic image 640 is selected for display at full resolution. The portion that is selected is sized so that the selected portion may be displayed at full resolution in the viewing pane 330. In FIG. 6, for example, the selection window 620 has approximately the same vertical to horizontal proportions as the viewing pane 330. In addition, the selection window 620 is sized so that a portion of the image covered by the selection window 620 substantially fills in the viewing pane 330 when displayed at full resolution.

In one embodiment, the viewer may move the selection window 620 to any portion of the viewing pane 330, such as by moving a mouse or pressing designated keys on a keyboard. Once the selection window 620 is over a portion of the image that the user would like to view at full resolution, the user selects the portion by pressing a button on the mouse or pressing a designated key on the keyboard, for example. In one embodiment, after selecting a portion for viewing at full resolution, the viewing pane 330 is updated to display the selected portion at full resolution in the viewing pane 330. After viewing the selected portion at full resolution for a predetermined period of time or until the user indicates, the viewing pane 330 is updated with the reduced resolution image 330, updated with an indication of the portion of the image that was viewed at full resolution. Alternatively, the viewing pane 330 may be sequentially filled with full resolution portions of the image without returning to the reduced resolution image.

FIG. 7 is the GUI 300 with a portion of a mammographic displayed at full resolution in the viewing pane 330. As noted above, many medical images, such as mammographic images, are taken at resolutions that are higher than resolutions of typical display and, thus, all pixel of these medical images may not concurrently be displayed. As illustrated in FIG. 7, a portion of a mammographic image is displayed at full resolution 710 in the viewing pane 330 of the GUI 300. The portion of the image displayed at full resolution in the viewing pane may be selected by the user (such as is described with reference to FIG. 6) or may be selected by the computing device according to predetermined display criteria.

In another embodiment, a viewing pane includes two panes, where a first pane, or selection pane, displays the image at a reduced resolution and a second pane, or display pane, displays at least a portion of the image at full resolution, or other user-defined display parameters. For example, a single display device could concurrently display an image such as the mammographic image 640 in the selection pane and a selected portion of the mammographic image 640 may be viewed in the display pane at full resolution, such as the full resolution image portion 710. In one embodiment, the selection pane may be sized to correspond to the size and shape that will accommodate a full resolution display pane. In one embodiment, the user may be provided with at least two methods of selecting portions of the reduced resolution image for viewing in the display pane. In particular, the user may move a selection window, such as the selection window 620 (FIG. 6), in the selection pane and the corresponding image area may be updated in the display pane. Alternatively, the user may use a pan function in the display pane and the position of the selection window in the selection pane is dynamically updated. In either case, areas that have been viewed at full resolution, or according to other user-defined display parameters, are dynamically adjusted so that they may be distinguished from the remaining portions. In an embodiment incorporating a selection and display pane, the relative sizes of the panes may be adjusted by the user or, alternatively, may be automatically adjusted by the software according to predetermined criteria.

In yet another embodiment, the selection pane may include multiple panes that each display a different image at a reduced resolution. For example, the multiple panes may display various images in a single image series. In one embodiment, the reduced resolution images are adjusted so that portions of the images that have been viewed at full resolution, or other user-defined display parameters, are visually distinguishable from the remaining portions. Accordingly, the display may provide an overview of the viewing status of multiple images.

The foregoing description details certain embodiments of the invention. It will be appreciated, however, that no matter how detailed the foregoing appears in text, the invention can be practiced in many ways. For example, the above-described pixel checking method may be performed on other types of images, in addition to medical images. For example, images of circuit boards, airplane wings, and satellite imagery may be analyzed using the described systems and methods for monitoring whether an image has been viewed according to predefined display parameters. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer-implemented method comprising:
   by a computing system including one or more hardware computing devices and a display device in communication with the one or more hardware computing devices, the one or more hardware computing devices configured with specific computer executable instructions,
      determining user-defined display parameters for display of an image on the display device, the user-defined display parameters associated with a user of the computing system;
      selectively displaying, in response to inputs by the user, regions of the image on the display device;
      storing tracking information indicating portions of the image that have been displayed on the display device according to the user-defined display parameters; and
      in response to determining, based on at least the stored tracking information and the user-defined display parameters, that a relevant portion of the image has not been displayed, providing a visible and/or audible notification to the user.

2. The method of claim 1, wherein the user-defined display parameters are associated with an identity or role of the user of the computing system.

3. The method of claim 1, wherein the user-defined display parameters indicate a percentage of pixels or portions of the image that must be displayed.

4. The method of claim 1, wherein the user-defined display parameters indicate one or more of an image window, a level, a brightness, a contrast, an opacity, or a color look-up table.

5. The method of claim 4, wherein the user-defined display parameters indicate more than one lung window or more than one bone window.

6. The method of claim 1, wherein the user-defined display parameters indicate one or more image processing functions.

7. The method of claim 6, wherein the one or more image processing functions include one or more of edge enhancement, automated image analysis, or computer-aided detection.

8. The method of claim 1, wherein the visible and/or audible notification indicates that at least the relevant portion of the image has not been displayed according to the user-defined display parameters.

9. The method of claim 8, wherein the visible and/or audible notification further indicates that at least a portion of the image that has been displayed according to the user-defined display parameters.

10. The method of claim 1, wherein the user-defined display parameters vary depending on one or more of a type of image, an area imaged, a clinical indication, a source of the image, the display device, and/or a user.

11. The method of claim 1 further comprising:
    receiving, by the computing system, input from the user adding to and/or removing portions of the image determined to be relevant by the computing system.

12. A system comprising:
    a display device configured to selectively display regions of an image;
    one or more hardware processors; and
    a computer readable medium operatively coupled to the one or more hardware processors, the computer readable medium storing software modules having executable instructions configured for execution by the one or more processors in order to:

determine a characteristic associated with the image to display;

determine required display parameters for display of the image, the required display parameters associated with the determined characteristic;

store tracking information indicating portions of the image that have been displayed on the display device according to the required display parameters; and in response to determining, based on at least the stored tracking information and the required display parameters, that a relevant portion of the image has not been displayed, provide a notification to a user of the system.

13. The system of claim 12, wherein the software modules have executable instructions further configured for execution by the one or more processors in order to:

determine the relevant portion of the image.

14. The system of claim 13, wherein the relevant portion of the image includes the entire image.

15. The system of claim 13, wherein the relevant portion excludes areas of the image that represent air.

16. The system of claim 12, wherein the required display parameters indicate more than one lung window or more than one bone window.

17. The system of claim 12, wherein the required display parameters indicate one or more image processing functions.

18. The system of claim 17, wherein the one or more image processing functions include one or more of edge enhancement, automated image analysis, or computer-aided detection.

19. The system of claim 12, wherein the image comprises one or more of a medical image, an image of a circuit board, an airplane wing image, or a satellite image.

20. A non-transitory computer readable medium storing software code configured for execution on a computer including one or more hardware processors, wherein the software code comprises modules including computer-executable instructions configured to at least:

determine a characteristic associated with an image to display on a display device of the computer;

determine required display parameters for display of the image on the display device of the computer, the required display parameters associated with the determined characteristic;

store information indicating portions of the image that have been displayed on the display device according to the required display parameters; and in response to determining, based on at least the stored tracking information and the required display parameters, that a relevant portion of the image has not been displayed, provide a notification to a user.

21. The non-transitory computer readable medium of claim 20, wherein the software code further includes computer-executable instructions configured to at least:

determine the relevant portion of the image.

* * * * *